United States Patent [19]
Lad et al.

[11] Patent Number: 5,834,655
[45] Date of Patent: Nov. 10, 1998

[54] CONTAMINATION TEXT

[75] Inventors: Devji Dalubhai Lad; Gordon Lethbridge; Paul Eric Linnett, all of Sittingbourne, United Kingdom

[73] Assignee: Shell oil Company, Houston, Tex.

[21] Appl. No.: 427,024

[22] Filed: Apr. 24, 1995

[30] Foreign Application Priority Data

Apr. 25, 1994 [EP] European Pat. Off. .............. 94302944

[51] Int. Cl.$^6$ ....................................................... G01N 1/00
[52] U.S. Cl. ......................... 73/863.21; 73/611.4; 436/29
[58] Field of Search ........................... 73/863.21, 863.25, 73/61.41; 436/29, 140

[56] References Cited

U.S. PATENT DOCUMENTS

| | | |
|---|---|---|
| 2,312,271 | 6/1943 | Smith . |
| 2,367,664 | 1/1945 | Campbell et al. . |
| 3,790,345 | 2/1974 | Mansfield et al. ..................... 23/230 R |
| 3,917,945 | 11/1975 | Sma et al. ................. 250/301 |
| 4,324,907 | 4/1982 | Senior et al. ........................... 560/185 |
| 4,992,379 | 2/1991 | Hanby . |
| 5,527,667 | 6/1996 | Ijzerman et al. ............................ 435/5 |

FOREIGN PATENT DOCUMENTS

| | | |
|---|---|---|
| 344950 | 12/1989 | European Pat. Off. . |
| 52/100285 | 8/1977 | Japan . |
| 89/08828 | 9/1989 | WIPO . |

*Primary Examiner*—Max H. Noori
*Attorney, Agent, or Firm*—Y. Grace Tsang

[57] ABSTRACT

A method for testing petroleum hydrocarbon contamination in which method a sample is mixed with an alkyl halide extraction solvent. Subsequently the solvent extraction phase is separated, and a Friedel-Crafts Lewis acid catalyst is added thereby obtaining a colored reaction product in the solvent extraction phase, the color of which being indicative of the petroleum hydrocarbon contamination.

6 Claims, No Drawings

CONTAMINATION TEXT

FIELD OF THE INVENTION

The present invention relates to a method for testing hydrocarbon contamination, particularly petroleum hydrocarbon contamination, in soil or water.

BACKGROUND OF THE INVENTION

In particular, the present invention relates to a method for testing petroleum hydrocarbon contamination in soil or water, which method comprises the steps of:

a. taking a sample,
b. adding an excess of an alkyl halide extraction solvent which is such that a solvent phase is obtained containing aromatic petroleum hydrocarbons separated from the sample,
c. separating the solvent extraction phase from the soil or water,
d. adding a Friedel-Crafts Lewis acid catalyst to obtain as reaction product a colored powder, and
e. measuring the color of the colored reaction product.

The color of the colored reaction product is indicative of the hydrocarbon contamination of the sample of soil or water.

Such a method is known from U.S. Pat. No. 4,992,379. In this method carbon tetrachloride is employed as alkyl halide extraction solvent. As Friedel-Crafts Lewis acid catalyst anhydrous aluminum chloride is added. This results in the formation of a colored reaction product which remains bound to the solid phase catalyst. Therefore, the colored reaction product settles to the bottom, and does not stay in the solvent phase. The color is indicative of the petroleum hydrocarbon contamination.

Although the above method provides a testing procedure which is quick and easy to use, certain shortcomings remain.

Firstly, identification and quantification are not always straightforward. The identification and quantification consist of comparing the above-mentioned colors with the photographs of standards. Sometimes the colors do not match.

Secondly, at the lower and upper end of the concentration range, the photographs of the standard curves lack definition making it extremely difficult to distinguish between the different concentrations by eye with any degree of certainty, thereby reducing the sensitivity and accuracy of the method quite considerably. To overcome the above problems, the colors produced in the solid phase in the above test could be measured by using a reflectance spectrophotometer. However, such portable instrument is not commercially available. This makes that the method cannot be used in the field. Thus, the usefulness of the test is severely limited.

As to testing samples of soil, it is a further problem that water contained in the soil reduces the efficiency of the solvent extraction leading to an underestimate of contamination levels.

It is considered yet a further problem that organic matter other than petroleum hydrocarbons contained in the soil sample can result in overestimation of contamination levels.

OBJECT OF THE INVENTION

Thus it is a main object of the present invention to provide a testing method allowing accurate qualification and quantification of hydrocarbon, particularly petroleum hydrocarbon, contaminants present in soil or water.

It is a further object of the present invention to arrive at a method adapted both for easy use and for accurately testing samples in the field.

DESCRIPTION OF THE EMBODIMENTS

Therefore in accordance with the present invention the method as mentioned above is characterized by adding an alkyl halide extraction solvent which is such that after the separating step and the Friedel-Crafts Lewis acid catalyst addition step results in the formation of a colored reaction product in the solvent extraction phase. This makes it easier to qualify and quantify the contamination.

In a preferred embodiment of the present invention the liquid alkyl halide extraction solvent substantially consists of dichloromethane.

When dichloromethane is used, the colored reaction product to be measured is formed in the liquid phase. It can be quantified by a portable spectrophotometer which is easy to use at contaminated sites resulting in accurately measured contamination levels.

It is further preferred to add a drying agent to a sample, prior to addition of the solvent. The drying agent can be anhydrous magnesium sulphate. Preferably, it is anhydrous sodium sulphate. The drying agent removes water, e.g. from the soil sample. This improves the extraction efficiency.

Certain types of polar organic matter can interfere with the test. Such organic matter will most often be found in soil samples. To remove this matter, a polar organic matter adsorbent is silica gel. Preferably aluminum oxide is employed for that purpose. Thus, possible erroneous influences on the final contamination levels are avoided in an advantageous way.

If water samples are tested, it can be advantageous to add a salting out agent before adding the extraction solvent. In an advantageous way said agent improves the efficiency of the extraction by forcing the petroleum hydrocarbons out of the water phase into the solvent phase. Preferably salts, such as sodium chloride are employed as salting out agent.

A preferred Friedel-Crafts Lewis acid catalyst is anhydrous aluminum trichloride.

The present method is effective for testing hydrocarbon contaminants, particularly petroleum hydrocarbon contaminants, more particularly aromatic petroleum hydrocarbon contaminants.

The present invention further provides a tool kit for testing hydrocarbon contamination, particularly petroleum hydrocarbon contamination, in soil or water, the kit comprising at least:

a sample container,
a measured amount of an alkyl halide extraction solvent and a Friedel-Crafts Lewis acid catalyst,
optionally, a graduated solvent extraction phase container, and
a portable spectrophotometer.

In a further embodiment of the tool kit, measured amounts of a salting out agent, a dehydrating agent, and a polar organic matter adsorbant are comprised.

In particular as spectrophotometer means a colorimeter is used.

The present method can be used for testing any kind of aqueous waste streams, ground-water, surface-water, and effluent streams containing contamination of hydrocarbons, particularly petroleum hydrocarbons.

The invention will be illustrated by the following illustrative embodiment which is provided for illustration purpose only and is not intended to limit the scope of the instant invention.

ILLUSTRATIVE EMBODIMENT

In order to obtain accurate petroleum hydrocarbon contamination levels the following procedure has been applied.

1. Weigh 5 g soil into a 50 ml screw-top glass container that can be sealed with a cap.
2. Mix the soil with approximately 5 g anhydrous sodium sulphate until the resulting mixture is free-flowing.
3. Add 20 ml dichloromethane (DCM) and shake for about 3 minutes.
4. Allow the soil to settle for 1 minute and remove 5 ml of the clear extraction solvent to a 10 ml screw-top glass test-tube.
5. Add about 0.1 g aluminum oxide and mix well for 1 minute.
6. Add about 0.1 g aluminum chloride and shake periodically for about 10 minutes.
7. Allow the aluminum salts to settle to the bottom of the tube before placing it into the sample holder of the spectrophotometer means and reading the absorbance of the yellow/brown color at 420 nm against a blank of DCM plus aluminum salts. The color is stable for at least 24 hours.
8. Convert the absorbance to concentration in the extraction solvent using the appropriate standard curve.
9. Convert the concentration in the extraction solvent to the concentration in the original soil sample.

The amounts of reagents as mentioned above are not critical. However, the reagents should be of very high purity (>99.9%)

The above procedure has been applied on a range of soil samples. The results are presented in the table below.

TABLE

| | | Petroleum hydrocarbon concentration (mg/kg soil) | | |
|---|---|---|---|---|
| Soil Type | Contamination | Lab method (IR) | Colorimetric | Conventional* |
| Sandy | Crude oil | 43,728 ± 932 | 44,400 ± 2,828 | 20,000–40,000 |
| Sandy | Crude oil | 4,618 ± 135 | 5,320 ± 57 | 2,000–4,000 |
| Clay | Diesel | 5,404 ± 458 | 4,812 ± 283 | 2,000–5,000 |
| Clay | Fuel oil | 1,913 ± 848 | 2,124 ± 147 | 500–1,000 |
| Clay | Fuel oil | 3,323 ± 266 | 3,158 ± 342 | 500–1,000 |
| Peaty | Unknown | 836 ± 24 | 818 ± 4 | 500–1,000 |

*method as described in U.S. Pat. No. 4,992,379.

As laboratory method a test in accordance with Environmental Petroleum Agency (USA) method EPA 418.1 (1978) was carried out.

A Hach DR 2000 (Hach is a trademark) spectrophotometer has been employed in the procedure mentioned above.

The limit of detection of the procedure in accordance with the present invention is 100 mg petroleum hydrocarbon contamination/kg (soil) for complex mixtures such as gasoline, diesel, and crude oil, and 10 mg contamination/kg (soil) for monoaromatic hydrocarbons such as benzene, toluene, xylene, and polyaromatic hydrocarbons such as naphthalene.

The appropriate standard curve is prepared prior to the series of tests.

From the above table it may be clear to those skilled in the art that very accurate data have been obtained by using the method in accordance with the present invention. The results as obtained by the method of U.S. Pat. No. 4,992,379 have been improved substantially using the method according to the present invention.

Further to the above it will be clear to a skilled person that depending on the level of contamination in the sample the solvent extraction phase can be diluted with an appropraite solvent, such as DCM, prior to carrying out the catalyst reaction in order to ensure that the absorbance falls within the linear range of the spectrophotometer used. Accordingly calculations of concentration have to be adapted.

As to samples of contaminated water, for example ground water, waste water or any kind of contaminated aqueous streams, 1 l of sample can be extracted with 20 ml of appropriate solvent.

In such an experiment the two phases can be separated advantageously in a separating funnel, allowing the lower solvent extraction phase to run into a solvent extraction phase container means preferably containing 5 g of anhydrous sodium sulphate to dry the sample prior to carrying out the color reaction and subsequent quantification.

We claim:

1. A method for testing hydrocarbon contamination in soil or water, which method comprising the following steps:
    (a) taking a sample of soil or water,
    (b) adding an excess amount of dichloromethane extraction solvent to extract hydrocarbon from the sample and obtaining a solvent extraction phase comprising the hydrocarbon extracted from the sample, wherein said petroleum hydrocarbon contains only hydrogen and carbon atoms and contains no polar non-hydrocarbon-atom-containing functional groups,
    (c) separating the solvent extraction phase from the soil or water,
    (d) adding a Friedel-Crafts Lewis acid catalyst and obtaining a colored reaction product of said hydrocarbon and said dichloromethane, wherein substantially all of said reaction product is soluble in the liquid dichloromethane solvent extraction phase, and
    (e) measuring the color of the colored reaction product solubilized in said liquid dichloromethane solvent extraction phase using a spectrophotometer.

2. A method for testing petroleum hydrocarbon contamination from soil or water, which method comprising the steps of:
    (a) taking a sample of soil or water,
    (b) adding an excess amount of dichloromethane to extract petroleum hydrocarbon from the sample and obtaining a solvent extraction phase comprising the petroleum hydrocarbon extracted from the sample, wherein said petroleum hydrocarbon contains only hydrogen and carbon atoms and contains no polar non-hydrocarbon-atom-containing functional groups,
    (c) separating the solvent extraction phase from the soil or water,
    (d) adding anhydrous aluminum trichloride and obtaining a colored reaction product of said hydrocarbon and said dichloromethane, wherein substantially all of said reaction product is soluble in the liquid dichloromethane solvent extraction phase and there is substantially no solid colored reaction product of hydrocarbon and dichloromethane present at the bottom of the dichloromethane solvent extraction phase, and (e) measuring the color of the colored reaction product solubilized in said liquid dichloromethane solvent extraction phase using a spectrophotometer, wherein the color is measured at 420 nm.

3. The method as claimed in claim 1, wherein the Friedel-Crafts Lewis acid catalyst is anhydrous aluminum trichloride, wherein in step (e) the color is measured at about 420 nm using said spectrophotometer, and wherein in step (d) there is substantially no solid colored reaction product of hydrocarbon and dichloromethane present at the bottom.

4. The method as claimed in claim 1, wherein said samples comprises soil, wherein said method further comprises a step of adding a dehydrating agent to the sample of soil after the sample has been taken in accordance with step (a).

5. The method as claimed in claim 4, further comprising a step of adding a polar organic matter adsorbant to the alkyl halide extraction solvent after separation from the soil in accordance with step (c).

6. The method as claimed in claim 1, wherein said sample comprises water, wherein said method further comprises a step of adding to the sample of water a salting out agent after the sample has been taken in accordance with step (a).

* * * * *